(12) United States Patent
Huang

(10) Patent No.: US 6,520,956 B1
(45) Date of Patent: *Feb. 18, 2003

(54) APPARATUS AND METHOD FOR PERFORMING LASER THERMAL KERATOPLASTY WITH MINIMIZED REGRESSION

(76) Inventor: David Huang, 1700 E. 13th St., Apt. 23EE, Cleveland, OH (US) 44114-3238

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/410,022

(22) Filed: Oct. 1, 1999

Related U.S. Application Data

(63) Continuation-in-part of application No. 08/744,936, filed on Nov. 6, 1996, now Pat. No. 6,033,396.
(60) Provisional application No. 60/007,316, filed on Nov. 6, 1995.

(51) Int. Cl.⁷ ........................... A61F 9/007; A61B 18/18
(52) U.S. Cl. ............................... 606/5; 606/10; 606/12; 606/13; 606/17
(58) Field of Search .................... 606/2, 3–17; 128/898

(56) References Cited

U.S. PATENT DOCUMENTS

| | | |
|---|---|---|
| 4,665,913 A | 5/1987 | L'Esperance, Jr. |
| 4,976,709 A | 12/1990 | Sand |
| 5,263,951 A | 11/1993 | Spears et al. |
| 5,281,211 A | 1/1994 | Parel et al. |
| 5,334,190 A | 8/1994 | Seiler |
| 5,348,551 A | 9/1994 | Spears et al. |
| 5,356,409 A | 10/1994 | Nizzola |
| 5,545,160 A | 8/1996 | O'Rourke |
| 5,779,696 A | 7/1998 | Berry |
| 5,782,822 A | 7/1998 | Telfair |
| 6,033,396 A | * 3/2000 | Huang et al. .................. 606/5 |

FOREIGN PATENT DOCUMENTS

| | | | |
|---|---|---|---|
| WO | 9201430 | * 2/1992 | ................ 606/11 |

OTHER PUBLICATIONS

Keates, R.H., et al., "Thermokeratoplasty for Keratoconus," Ophthal. Surg., vol. 6, No. 3, Fall 1975, pp. 89–92.

(List continued on next page.)

*Primary Examiner*—David M. Shay
(74) *Attorney, Agent, or Firm*—Fleshner & Kim, LLP

(57) ABSTRACT

Apparatus and method for preforming laser thermal keratoplasty capable of treating treatment areas with shapes that reduce regression. Both contact and non-contact apparatuses and methods are provided. The apparatus includes laser sources, a projection optical system, observation system, and control system. In some embodiments, the projection system uses two steering mirrors or a mask to control laser beam position on the cornea. This projection system enables precise control of the area of corneal heat shrinkage using relatively low-powered lasers, such as diode lasers. Desired changes in corneal refractive power are produced by selected patterns of photothermal shrinkage of corneal collagen tissue. The selected patterns are arrangements of oblong shapes that are preferably tapered at the ends of the long axis. The oblong shape and tapering distribute tension in the cornea over a wider area of collagen shrinkage and improve the stability of refractive correction. The long axes of the oblong treatment areas are preferably oriented radially for hyperopia correction and circumferentially for astigmatism correction.

23 Claims, 9 Drawing Sheets

OTHER PUBLICATIONS

Peyman, G.A., et al., "Modification of Rabbit Corneal Curvature With Use of Carbon Dioxide Laser Burns," Ophthal. Surg., vol. 11, No. 5, May 1980, pp. 325–329.

Seiler, T., et al., "Laser Thermokeratoplasty by Means of a Pulsed Holmium:YAG Laser for Hyperopic Correction," Refract. & Corn. Surg., vol. 6, Sep./Oct. 1990, pp. 335–339.

Anderson, R.R., et al., "Selective Photothermolysis: Precise Microsurgey by Selective Absorption of Pulsed Radiation," Science, vol. 2, Apr. 1983, pp. 524–527.

Moreira, H., et al., "Holmium Laser Thermokeratoplasty," Ophthal., vol. 100, No. 5, May 1993, pp. 752–761.

* cited by examiner

APPARATUS AND METHOD FOR PERFORMING LASER THERMAL KERATOPLASTY WITH MINIMIZED REGRESSION

This is a continuation-in-part of U.S. patent application Ser. No. 08/744,936, filed Nov. 6, 1996, U.S. Pat. No. 6,033,396 which claims the benefit of U.S. Provisional Application No. 60/007,316, filed Nov. 6, 1995.

BACKGROUND OF THE INVENTION

1. Field of the Invention

This invention relates to the correction of hyperopia, astigmatism, and irregular optical aberrations by changing the shape of the cornea. Specifically, it relates to laser thermal keratoplasty (LTK), where a laser beam is used to heat selected areas of the cornea and cause local shrinkage.

2. Background of the Related Art

Various methods of changing corneal curvature have been developed. In incisional keratotomy, radial, arcuate, or other patterns of incision are made on the corneal surface. These incisions weaken the structural integrity of the cornea and can result in daily refractive fluctuation and long-term refractive shift. Furthermore, surgical errors can result in corneal penetration and intraocular infection.

In mechanical keratomilieusis procedures, a mechanical means is used to remove corneal tissue in the central optical zone. These methods have poor predictability in both the correction of myopia and hyperopia, and can result in severe surgical complications.

In photorefractive keratectomy (PRK), a laser is used to ablate corneal tissue in the central optical zone. A major shortcoming of PRK is the development of haze in the central optical zone. Another shortcoming of PRK is the relatively poor results in the treatment of hyperopia; regression is severe unless a large area of the cornea is ablated. Unlike methods mentioned above, thermal keratoplasty does not involve the undesirable complications relating to incision or excision of corneal tissue.

In thermal keratoplasty, heat is applied to portions of the corneal stroma to produce collagen shrinkage. Corneal stromal collagen is known to shrink to approximately one third of its original length when heated to a temperature range of 60° C. to 65° C. At higher temperatures, substantial additional shrinkage does not occur, but thermal injury and necrosis may result. Heat can be applied to the cornea with surface probes, penetrating probes, electrical probes, ultrasound, and laser light. Laser heating is the ideal choice because the magnitude, depth and pattern of heating can be more precisely controlled and rapid noncontact application is possible.

Several methods of laser thermal keratoplasty (LTK) have been described. The earliest patent concerning laser LTK, issued to Sand (U.S. Pat. No. 4,976,709) taught the use of optical radiations in the wavelength range of 1.8 to 2.55 microns for the shrinkage of collagen tissues. It also specified the use of laser radiation with corneal-collagen absorption coefficient of 15 to 120 cm$^{-1}$ for keratoplasty. It was taught that a pulsed application of about 100 msec duration is preferable. Sand further taught the use of means for measuring corneal shape before and after application of laser energy to determine the desired and resulting alteration in corneal refraction. It described experiments using circular or linear arrays of circular dots. Sand further taught the use of various chemical agents to reduce the threshold shrinkage temperature of tissue. In the Sand series of patents, block diagrams of a laser delivery system were provided, but no specific optical arrangement or method of operation was described.

U.S. Pat. No. 5,263,951 to Spears, et al. taught the use of a laser delivery system that engages the cornea and produces a variety of irradiation patterns for correcting myopia and hyperopia. The patterns described include patterns of central disk, annular rings, radial lines, and round dots. The patent presents data obtained using a Co:MgF$_2$ laser that produced 0.5 to 2.0 W continuous-wave output. However, in the data presented, much higher powers were used, see, for example, in line 2 of Table C of the patent, 5.3 Diopters of hyperopic correction was produced with an annular pattern with 7 mm outer diameter and 5 mm inner diameter with a fluence level of 1.0 Joules/mm$^2$ delivered in 1.0 second. This translates to a 38 W laser power. Furthermore, the data described was markedly inefficient compared to results described in Moreira, et al., Holmium Laser Thermokeratoplasty, *Ophthalmology*, Vol. 100, pp. 752–761, 1993.

In Moreira, et al., a similar 6 mm diameter circular treatment pattern using 32 spots of 410 micron diameter and 9 Joules/cm$^2$ produced 7 diopters of hyperopic correction. This means in Moreira, et al. only 1% of the energy used in U.S. Pat. No. 5,263,951 was used, yet resulting in greater refractive correction.

U.S. Pat. No. 5,348,551 to Spears describes an apparatus similar to U.S. Pat. No. 5,263,951, with the difference in that the intended effect of irradiation is keratocyte killing rather than collagen shrinkage. The data presented in the patent show highly variable results in a rabbit study.

U.S. Pat. No. 5,334,190 to Seiler taught the use of a contact laser probe for the delivery of focused laser energy onto the cornea to cause collagen shrinkage. This contact probe limits the irradiation pattern to a series of round dots.

U.S. Pat. No. 5,281,211 to Parel, et al. taught the use of a noncontact laser delivery system for LTK that utilized axicon optics to form a pattern of circular laser spots on the cornea.

In general, the laser delivery systems previously described can be divided into two categories, contact and noncontact. Noncontact delivery is easier to apply, faster and more comfortable for the patient. Of the prior art patents, only U.S. Pat. No. 5,281,211 to Parel, et al. provides an optical system for noncontact delivery. In U.S. Pat. No. 5,281,211, the treatment laser beam is projected simultaneously to a pattern of several treatment areas on the cornea. Consequently, a high laser power output is necessary to achieve the desired corneal stromal heating before significant heat diffusion out of the irradiated area occurs. This precludes the use of diode lasers because diode lasers of suitable wavelengths for LTK currently do not possess the required high peak powers. Nevertheless, diode lasers are attractive light sources because of their low cost, compactness and reliability. A cw InGaAsP/InP diode laser that is capable of emitting 0.5 W at 1.8–1.96 micron wavelength is currently available (SDL-6400, SDL Inc., San Jose, Calif.). This range of wavelength has absorption lengths in water in the range of the typical human corneal thickness, which is highly desirable for LTK. However, a noncontact LTK system that can operate with only 0.5 W of laser power has not been previously described.

It is generally acknowledged that the regression of refractive changes is the main drawback of LTK at this time. The desired refractive change of LTK has been reported to undergo large regression over a period of months.

Despite evolutionary improvements in LTK methodology, significant regression still occurs in all dot patterns of LTK reported so far. The currently available commercial LTK systems from Summit, Sunrise and Technomed all use a ring or concentric rings of laser dot heating, which do not optimally distribute the heating in the corneal stroma to reduce stress concentration. Thus an improved pattern of laser application is needed to optimize the stability of LTK results.

The above references are incorporated by reference herein where appropriate for appropriate teachings of additional or alternative details, features and/or technical background.

SUMMARY OF THE INVENTION

It is an object, therefore, of the invention to provide both contact and noncontact apparatuses and methods for performing laser thermokeratoplasty that are capable of reducing regression of the intended refractive correction.

Another object of the invention is to provide patterns of laser application for LTK that improve the distribution of tension in the treated portion of corneal stroma and thereby improve the stability of refractive correction.

Another object of the invention is to provide an automated scanning of laser treatment patterns on the cornea for the correction of hyperopia, astigmatism, and irregular optical aberrations of the eye.

Another object of the invention is to provide noncontact apparatus and method of laser thermokeratoplasty that require less laser power than previously described noncontact apparatuses.

Another object of the invention is to provide to provide noncontact apparatus and method of laser thermokeratoplasty that uses a diode laser.

The above objects are achieved by an apparatus for performing laser thermal keratoplasty on an eye of a patient to achieve an intended refractive correction, which includes a treatment laser which outputs a treatment beam; scanning unit for scanning said treatment beam; and controlling and processing units coupled to said scanning means for controlling said scanning unit in a predetermined manner so that said treatment beam is scanned over a treatment area, the shape of said treatment area reducing regression of the intended refractive correction.

The above can be further achieved when said treatment area comprises tapered ends, and/or the treatment area optimizes stress distribution in the cornea of the eye. Some treatment area shapes to achieve this are an oblong shape, a spindle and a crescent shape.

The treatment laser might preferably output a treatment beam having a wavelength such that collagen shrinkage in a majority of the thickness of the cornea occurs. Examples of such laser is a diode laser.

The above and other objects are also achieved by an apparatus for enabling a doctor to perform laser thermal keratoplasty on an eye of a patient, to achieve an intended refractive correction, including: optical beam output unit for outputting a treatment beam and a visible alignment beam aligned to yield a combined beam, dual focusing beams, and a central fixation beam to the eye of the patient, wherein said treatment beam can be selectively turned on or off; beam position adjusting unit for adjusting position of said optical beam output unit with respect to the eye of the patient; optical observation unit for viewing said visible beam, dual focusing beams, and central fixation beams on the eye of the patient, whereby said beam position adjusting unit is adjusted with respect to the eye of the patient until the dual focusing beams intersect so that they appear to be a single spot on the cornea; scanning unit for scanning said treatment beam; and controlling and processing unit coupled to said scanning unit for controlling said scanning unit in a predetermined manner so that said treatment beam is scanned over a treatment area, the shape of said treatment area reducing regression of an intended refractive correction.

The treatment laser is preferably a laser with a wavelength that has an absorption length in corneal tissue that is between 200 to 800 microns. These absorption lengths can be found in the wavelength range between 1.3 to 3.3 microns. The treatment laser can be a cw InGaAsP/InP diode laser which is preferably tuned for emission at approximately 1.87 micron wavelength and more generally in the 1.86–1.89 wavelength range. Other continuous wave and pulsed lasers may also be used. For pulsed lasers, the pulse repetition rate is preferably sufficiently rapid such that the scanned laser spots overlap to form a confluent pattern.

The projection unit preferably comprises collimation optics, optics for focusing laser beams onto the cornea, beam path relay optics, and scanning unit for scanning or steering laser beams to form two-dimensional treatment patterns on the cornea. The steering unit preferably comprises a pair of galvanometer-driven mirrors that control the position of laser beams on the cornea in two orthogonal dimensions.

The apparatus preferably includes unit for projecting a visible laser beam onto the cornea substantially coincident with the position of the treatment laser beam. The aiming laser beam and the treatment laser beam are preferably mixed by using a wavelength-selective mirror. The apparatus preferably also includes unit of projecting visible beams for focusing and unit for projecting a visible beam as a fixation target. Preferably, the unit for controlling the treatment laser projection include a computer with a user input unit enabling the user to control the scanning unit and the output level of the treatment laser which in turn controls the angulation of the treatment and visible beams.

The above and other objects are further achieved by the provision of a method for performing laser thermal keratoplasty on an eye of a patient, to achieve an intended refractive correction, including the steps of: selecting treatment areas based on patient problem information, the shape of which is selected to minimize regression of the intended refractive correction; outputting a treatment beam from a treatment laser; and scanning said treatment beam over said treatment areas.

The above and other objects are further achieved by the provision of a method for performing laser thermal keratoplasty on an eye of a patient, comprising the steps of: outputting a treatment beam and a visible alignment beam aligned to yield a combined beam, dual focusing beams, and a central fixation beam from a beam output unit to the eye of the patient, wherein said treatment beam can be selectively turned on or off; adjusting position of said optical beam output unit with respect to the eye of the patent, said visible beam, dual focusing beams, and central fixation beams on the eye of the patient; viewing said visible beam, dual focusing beams, and central fixation beams on the eye of the patient until the dual focusing beams appear to be a single beam while the patent is affixed to said central fixation beam; and scanning over a treatment area, the shape of said treatment area reducing regression.

According to the present invention, the pattern of corneal irradiation preferably comprises one or more oblong areas of laser heating. The ends of the oblong areas are preferably tapered. The resulting shape may be called "spindle-shaped" or "elliptically-shaped." If the long axis of the laser treatment area is curved, it is termed "crescent-shaped." The treatment areas are preferably formed by a pattern of lines of equal width scanned on the cornea.

According to the present invention, a preferred method for hyperopia correction is to use a circular group of radially-oriented spindle-shaped treatment areas placed an equal distance apart. For the correction of regular astigmatism, a preferred method is to use one or more pairs of treatment areas placed at equal distances from the center on the minus cylinder axis of the manifest refraction. For astigmatism correction, the long axes of the treatment areas are preferably oriented circumferentially. For the correction of corneal irregular optical aberration due to local ectasias, the area of irradiation is preferably placed on or near the area of greatest corneal ectasia.

According to the present invention, some of the preferred methods of thermal keratoplasty are performed by using a mask to position a laser probe relative to the eye. In some of these methods, the laser probe comes into contact with the eye.

The above and other objects or advantages and features of the invention will become more apparent from the following description thereof taken in conjunction with the accompanying drawings.

Additional advantages, objects, and features of the invention will be set forth in part in the description which follows and in part will become apparent to those having ordinary skill in the art upon examination of the following or may be learned from practice of the invention. The objects and advantages of the invention may be realized and attained as particularly pointed out in the appended claims.

BRIEF DESCRIPTION OF THE DRAWINGS

The invention will be described in detail with reference to the following drawings in which like reference numerals refer to like elements wherein.

DETAILED DESCRIPTION OF PREFERRED EMBODIMENTS

The speed and amount of regression after LTK is related to the concentration of tension in the small area of shrunken stromal collagen, which induces stromal remodeling. There are several evidences supporting this, including the following.

(a) Regression is more pronounced when heating is applied only to the superficial layer of the cornea. Early attempts at thermal keratoplasty using surface heat probes met with prompt regression of the treated cornea to pre-treatment keratometric readings (Keats R H, Dingle J. Thermokeratoplasty for keratoconus, *Ophthalmic surgery* 1975; Vol. 6, pp. 89–92). LTK with a $Co_2$ laser with a shallow absorption length of 25 microns resulted only in transient change in refraction (Peyman G A, Larson B., Raichand M., Andrews A H, Modification of rabbit corneal curvature with the use of carbon dioxide laser burns, *Ophthalmic surgery* 1980; Vol. 11, pp. 325–329). A Holmium YAG laser, which is able to heat the anterior and mid-stromal regions, produced more lasting refractive changes. However, marked decrease of refractive change still occurs in a period of a few months (Seiler, T. Ho: YAG laser thermokeratoplasty for hyperopia, *Ophthalmology Clinic of North America* 1992; Vol. 4, pp. 773–780, and Seiler T., Matallana M., Bende T., Laser thermokeratoplasty by means of a pulsed holmium: YAG laser for hyperopic correction, *Refractive & Corneal Surgery* 1990; Vol. 6, pp. 335–339).

(b) LTK for the treatment of secondary hyperopia after PRK provides more stable results than LTK for primary hyperopia. This is due to the removal of Bowman's layer and some anterior stroma in the central cornea, which reduces the restorative tension on the LTK treatment area and reduces regression.

(c) LTK with a double ring of laser dots creates more stable refractive changes for larger amounts of intended correction. Furthermore, when the double ring of dots are aligned radially rather than staggered, the results are more stable. The aligned double rings of dots distribute the restorative tension over a larger stromal area and therefore has less tendency to regress.

(d) LTK for astigmatism has so far uniformly met with rapid regression of results. Current methodology treats two small circular areas of the cornea on an astigmatic axis. The resulting tension is concentrated on the two small areas and causes rapid regression.

Figure 1:
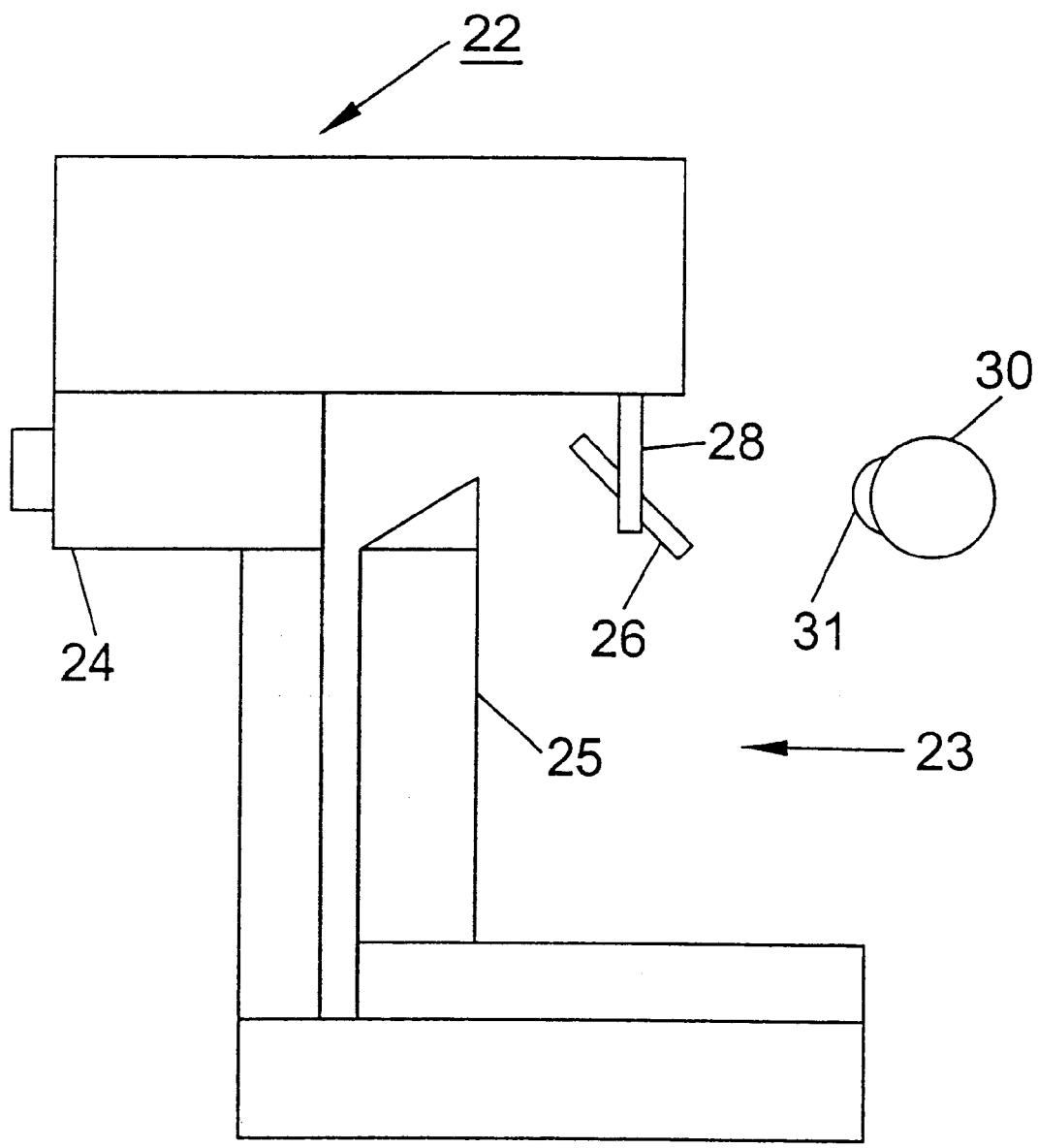
FIG. 1 is a side view schematic diagram of a preferred embodiment of the apparatus of the present invention.

FIG. 1 is a side view schematic diagram of a preferred embodiment of the apparatus of the present invention which reduces regression by providing treatment areas of specified shapes, orientations, sizes and locations. Further explanation of this will be explained in Laser generating and projection apparatus 22 is connected to a biomicroscope 23. Biomicroscope 23 preferably comprises an illumination apparatus 25 and an optical observation apparatus 24. Preferably biomicroscope 23 is a slitlamp biomicroscope familiar to those skilled in the clinical examination of eyes. Alternatively, a video imaging system can be used.

According to FIG. 1, slitlamp illumination from slit source 25 passes through wavelength-selective mirror 26 and reaches cornea 31 of eye 30. Laser beams from laser apparatus 22 are reflected by a wavelength-selective mirror 26 and thereby directed toward cornea 31 of eye 30. Mirror 26 is connected to main body of laser apparatus 22 by connecting strut 28.

The present invention provides for a means of observing and adjusting the alignment of laser beams with respect to the eye to be treated. In a preferred embodiment diagramed in FIG. 1, biomicroscope 23 provides illumination and magnified binocular view of subject eye 30. Corneal projections of visible laser beams from apparatus 22 are viewed through biomicroscope 23. Apparatus 22 is rigidly attached to the optical observation apparatus 24 and both apparatuses move as one unit. Preferably, apparatus 24 provides for a means for finely adjusting its vertical, horizontal and axial position by the use of a sliding beam and a rotary height adjustment knob which are commonly found in clinical slitlamp biomicroscopes. To position eye 30, preferably the subject's head is stably positioned using chin and forehead rests commonly found in clinical slitlamp biomicroscopes.

Figure 2:
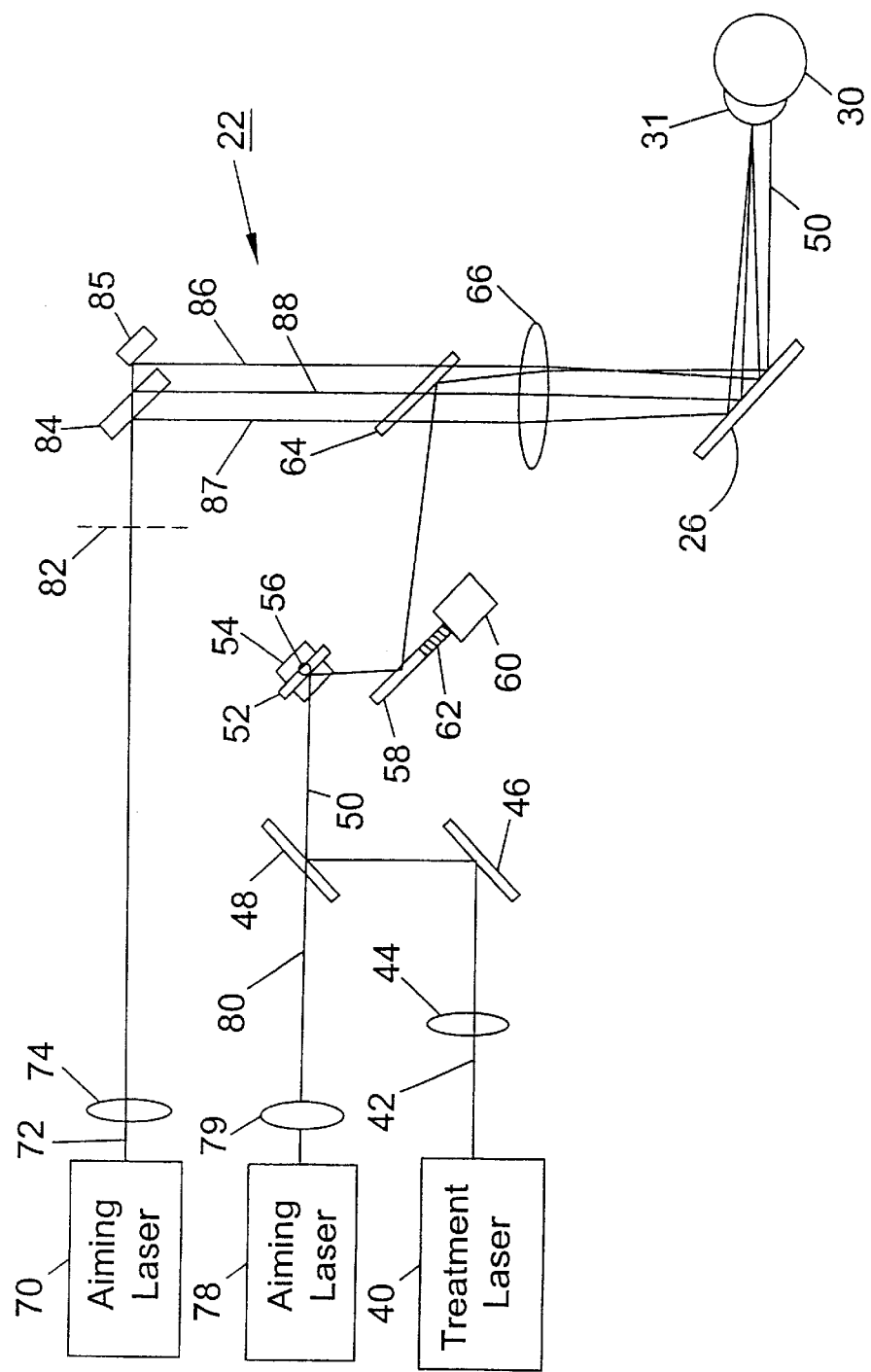
FIG. 2 illustrates the optical arrangement of the laser apparatus of a preferred embodiment of the present invention.

FIG. 2 illustrates the optical arrangement of the laser apparatus 22 of a preferred embodiment of the present invention. Output beam 42 of treatment laser 40 is collimated by optics 44. In the case where laser 40 is an internal cavity diode laser, optics 44 preferably comprises a combination of anamorphic prisms and lenses. Anamorphic prisms and astigmatism compensation optics are necessary to correct the asymmetric radiation pattern inherent in an internal cavity diode laser such that the beam 42 is eventually focused to a round spot on cornea 31. In the case where laser 40 has a symmetric beam profile, optics 44 may be a simple lens. Beam 42 is reflected by mirror 46 toward wavelength-selective mirror 48. Mirror 48 mixes treatment beam 42 with visible alignment beam 80 into a combined beam 50. Beam 50 is deflected in turn by steering mirrors 52 and 58 which are driven by steering means 54 and 60. Mirrors 52 and 58 are connected to the steering means 54 and 60 by drive shafts 56 and 62. Steering means 54 and 60 are preferably galvanometers. Alternatively, steering means 54 and 60 may comprise stepper motors or other means. The axis of rotation of mirror 52 is perpendicular to the page. This rotation controls the vertical position of beam 50 relative to cornea 31. The axis of rotation of mirror 58 is along shaft 62 and this rotation controls the horizontal position of beam 50 relative to cornea 31. After mirror 58, beam 50 is reflected by wavelength-selective mirror 64 and focused by lens 66. In order to focus beam 50 onto cornea 31, the optical distance between lens 66 and cornea 31 is preferably substantially the focal length of lens 66. In order to keep the axis of beam 50 downstream of lens 66 substantially parallel to the central optical axis, the average optical distance between the steering mirrors 52/58 and lens 66 is also preferably substantially the focal length of lens 66. When beam 5 is substantially parallel to the central optical axis, small focusing error does not produce significant beam position error at cornea 31. Mirror 64 is preferably highly reflective at the wavelength of treatment laser 40, partially reflective at the wavelength of aiming laser 78, and partially transmissive at the wavelength of the aiming laser 70. Finally, beam 50 is reflected by wavelength-selective mirror 26 onto cornea 31 of eye 30. Mirror 26 is preferably highly reflective at the wavelength of treatment laser 40 and partially reflective at visible wavelengths.

Referring to FIG. 2, output beam 72 of visible-wavelength aiming laser source 70 is focused by lens 74 onto retinal conjugate plane 82. The distance between plane 82 and lens 66 is substantially the focal length of lens 66. Beam 72 is split by beam splitter 84 and mirror 85 into dual focusing beams 86 and 87 and a central fixation beam 88. Beams 86–88 are partially transmitted by mirror 64 and collimated by lens 66. Mirror 26 reflects beams 86–88 toward cornea 31. To place the focus of treatment beam 42 on cornea 31, the laser surgeon moves LTK apparatus 22 until dual beams 86 and 87 converge on the central cornea. Fixation beam 88 approaches eye 30 along the central optical axis of laser apparatus 22. The patient is instructed to fixate on beam 88 so that the visual axis of the subject eye 30 is parallel to the axes of beam 88. To properly center the laser projection pattern, the laser surgeon then moves laser apparatus 22, until the corneal reflections of beams 86–88 are centered on the pupil aperture of eye 30.

Again referring to FIG. 2, output beam 80 of a second aiming laser 78 is collimated by lens 79. Aiming lasers 70 and 78 are preferably of different colors. Beam 80 is transmitted by wavelength-selective mirror 48 and coaxially mixed with treatment beam 42 into combined beam 50. All aiming beams, which are beams 86, 87, 88 and 80, are of low enough power when they reach eye 30 to be safe for extended retinal exposure.

Figure 3:
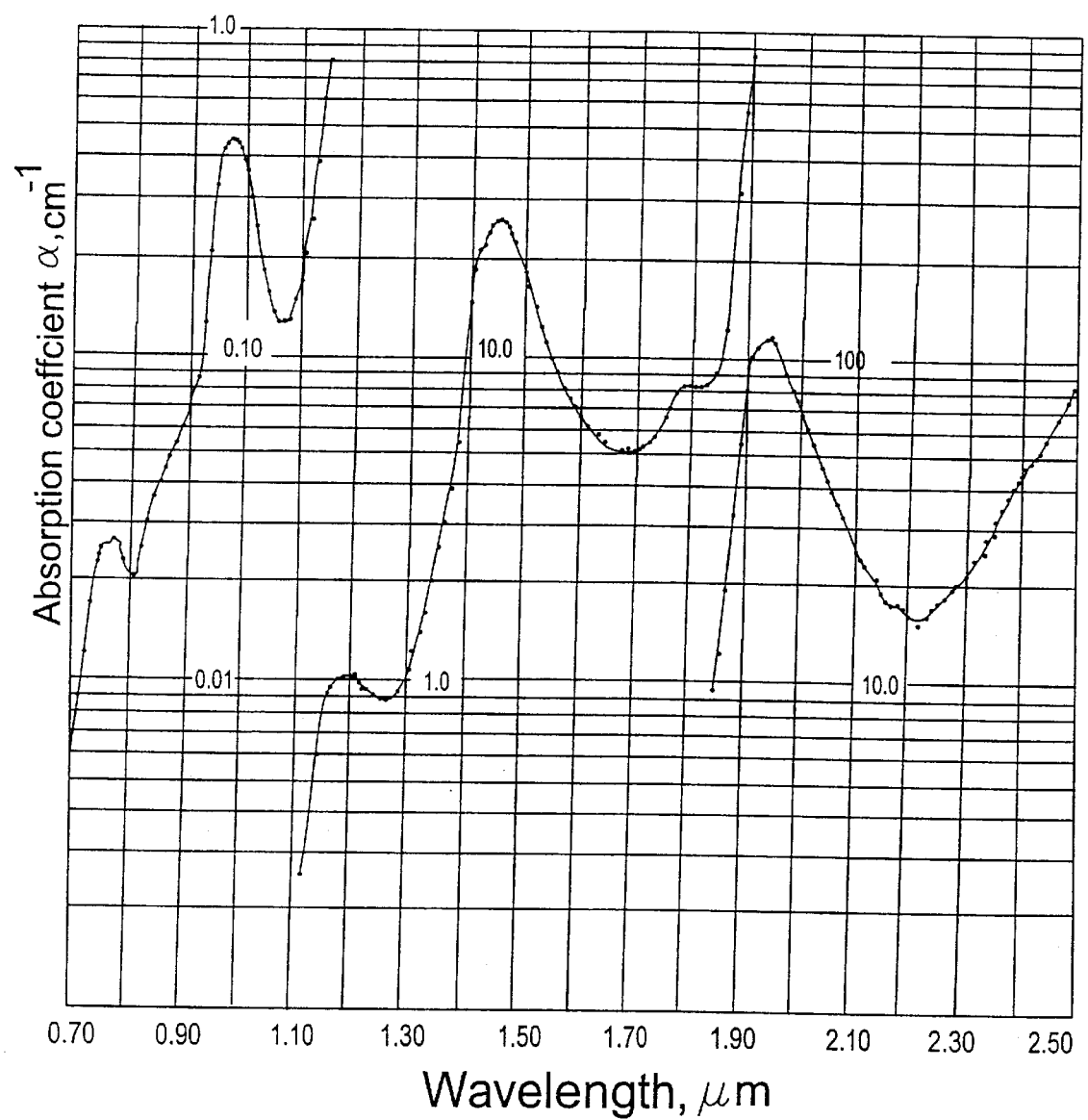
FIG. 3 is a plot of the absorption coefficient of water as a function of optical wavelength in the near infrared range.

Treatment laser 40 is preferably of a wavelength that has an absorption length in corneal tissue of between 200 to 800 microns. Usable infrared wavelength range is found between 1.3 to 3.3 microns. The relationship between absorption length in water and optical wavelength in the near infrared spectrum is plotted in FIG. 3. FIG. 3 is taken from W G Driscoll, W. Vaugh, *Handbook of Optics*, McGraw-Hill, pp. 15–28, 1978. The laser generating means is preferably a laser diode, preferably a cw InGaAsP/InP diode laser. The InGaAsP/InP laser is tunable in the 1.8--1.96 micron wavelength range. According to the present invention, the diode laser is preferably tuned for emission in the 1.86–1.89 micron wavelength range, where the corresponding absorption length in water ranges between roughly 800 microns to 200 microns. More specifically, the diode laser is preferably tuned to approximately 1.87 micron wavelength, where the water absorption length is substantially 500 microns. The 500 micron absorption length is preferable to the approximately 400 micron absorption length of the 2.1 micron wavelength holmium lasers. In holmium laser LTK, better results were achieved using multi-pulse application of laser energy so that deeper heating of the corneal stroma could occur through heat diffusion. Corneal endothelial damage in holmium laser LTK has been negligible at adequate treatment fluences. Thus deeper stromal heating without endothelial damage can be achieved by using an absorption length longer than that of holmium LTK. Besides the advantage of being tunable to wavelengths with optimal absorption lengths, the diode laser is also preferable because of its compactness, low costs, and reliability. For simplicity, the diode laser is preferably an internal cavity laser tuned by controlling the reflective coatings on the output facets, diode internal structures, operating currents, and temperature. Alternatively, an external cavity and etalon(s) can be used to control the diode laser wavelength. The treatment laser may also be other continuous wave or pulsed lasers with an absorption length in the preferred range. The holmium laser with output at approximately 2.1 microns wavelength and the Co:Mg:F2 laser with tunable output between 1.55–2.25 microns are both suitable. A further alternative is a frequency-halved Nd:YAG laser at 2.1 micron wavelength. For pulsed lasers, the pulse repetition rate is preferably rapid enough for the scanned laser spots to overlap and form a confluent pattern.

Figure 4:
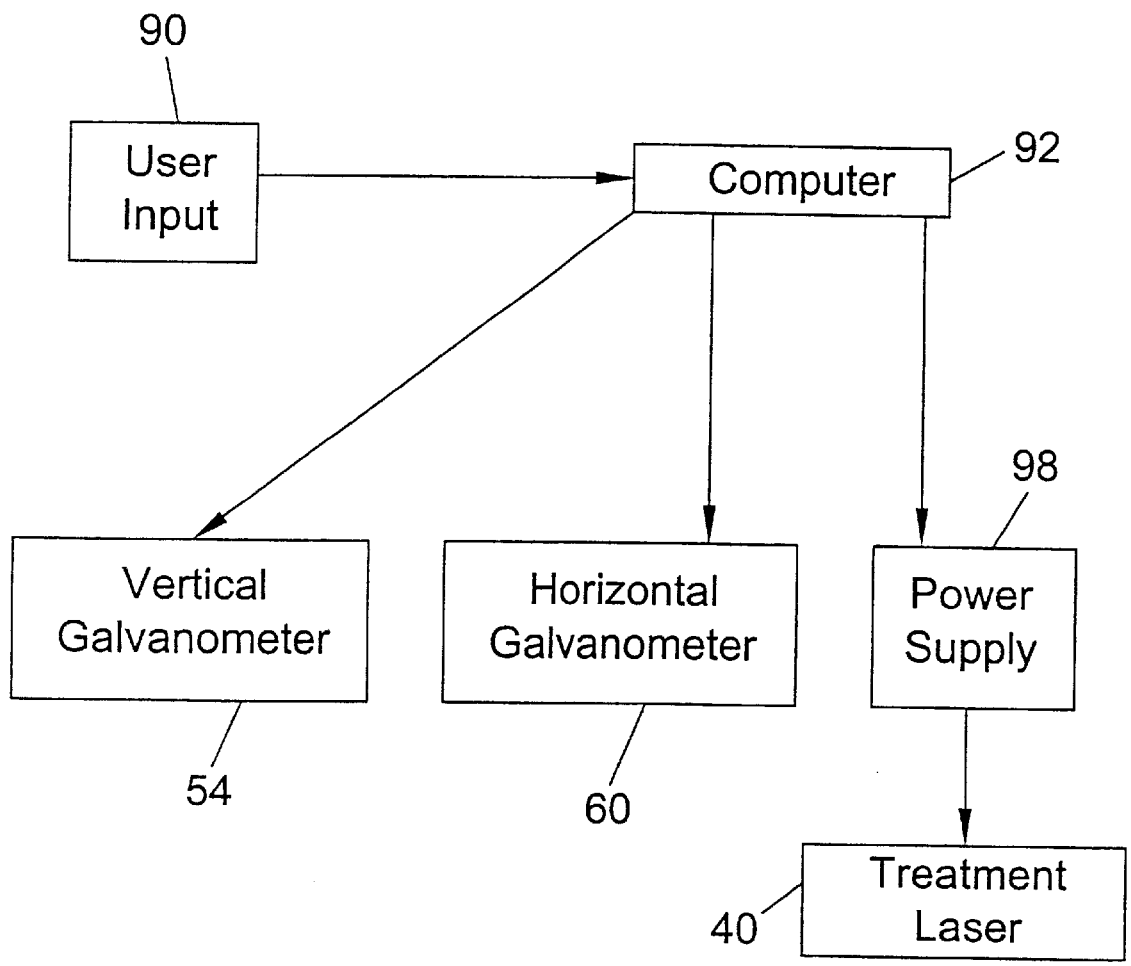
FIG. 4 is a block diagram of the control system of a preferred embodiment of the present invention.

Referring to FIG. 4, the laser system of the present invention is preferably controlled through a computer 92. User input devices 90 are used to enter parameters of the laser treatment and control the initiation and possible interruption of treatment. Input devices 90 preferably comprise a key board, a pointing device such as a mouse, and a foot peddle actuation switch. Other input means may also be used. Computer 92 controls the mirror steering means 54 and 60 and power supply 98 of treatment laser 40. Power supply 98 controls the output level of laser 40.

In preferred embodiments, the movement of the eye can be tracked by a video tracking system, a laser tracking system, or other tracking devices.

Figure 5A:
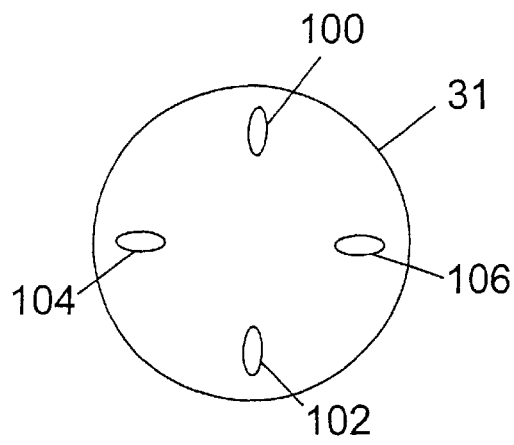
FIG. 5A illustrates a treatment pattern for the correction of hyperopia according to the teachings of the present invention.
Figure 6:
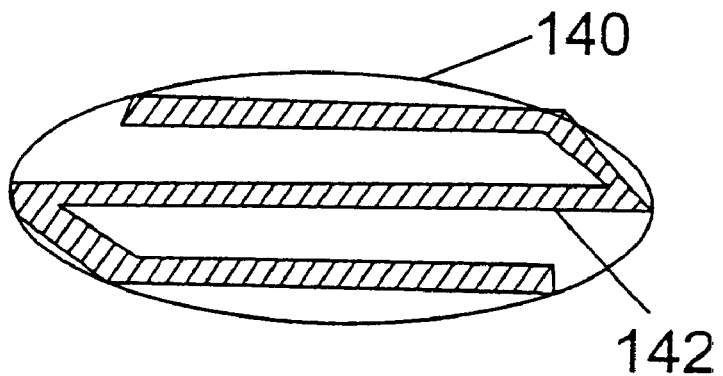
FIG. 6 illustrates a preferred method to scan a spindle-shaped treatment area according to the teachings of the present invention.

FIG. 5A illustrates a treatment pattern for the correction of hyperopia according to the teachings of the present invention. Treatment laser beam 42 is applied to cornea 31 in evenly-spaced areas arranged in a circular pattern. The number of treatment areas preferably ranges between 4 and 16. However, a number as low as 3 or 2, or arbitrarily high may be used. In FIG. 5A, four treatment areas 100, 102, 104 and 106, are shown. The treatment areas for hyperopia are preferably spindle-shaped with the long axes oriented radially. Referring to FIG. 6, the spindle shape is oblong with tapered ends on its long axis. In the treatment areas, laser heating of the cornea stroma and Bowman's layer causes local shrinkage of collagen. Shrinkage of the treatment area causes a change in the cornea shape. Referring to FIG. 5A, the circular arrangement of the treatment areas cause a belt-like effect on the mid-peripheral cornea, causing central corneal steepening and myopic shift. Regression is caused by gradual circumferential stretching of the treatment area from restorative circumferential corneal tension. In prior art methods of LTK hyperopia correction, these treatment areas are generally small circular spots, causing concentration of circumferential tension on the central portion of the spots. The stressed area undergoes corneal remodeling and results in regression of the desired refractive changes. According to the present invention, the oblong shape of the treatment area spreads the restorative corneal circumferential tension over the longer axis. This reduces the stress on the heat-shrunken collagen and decreases regression of refractive correction. Furthermore, according to the present invention, the tapering at the ends of the spindle-shaped treatment areas eliminates the stress from abrupt tissue distortion at the junction of treated and untreated areas. This further reduces regression. Those skilled in the art of surgery in general, would appreciate that in closing a wound associated with tissue excision, the tension of wound closure is greatly reduced by excising tissue in the shape of a spindle or ellipse. A similar principle is applied here. Thus the advantages of the spindle-shaped treatment area of the present invention are apparent.

The amount of hyperopia correction is primarily controlled by several parameters: (a) the width of the treatment areas, (b) the number of treatment areas, and (c) the distance between the center of the cornea and the treatment areas. Greater width and larger number of treatment areas create greater tightening of the circumferential belt and greater central corneal steepening. The lengths of the treatment areas are proportionally increased for wider and more numerous treatment areas to reduce regression. Smaller distances between the treatment patterns and the center moves the circumferential melting effect closer to the center and also produces greater central corneal steepening and hyperopia correction.

Figure 5B:
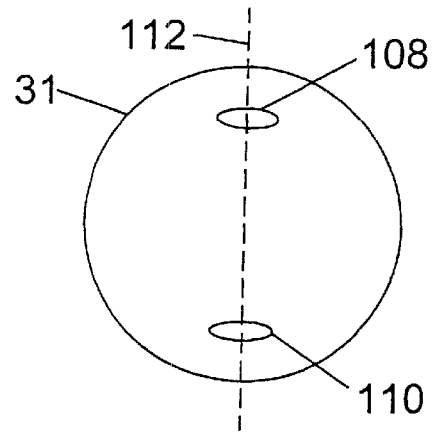
FIG. 5B illustrates a treatment pattern for the correction of astigmatism according to the teachings of the present invention.
Figure 7:
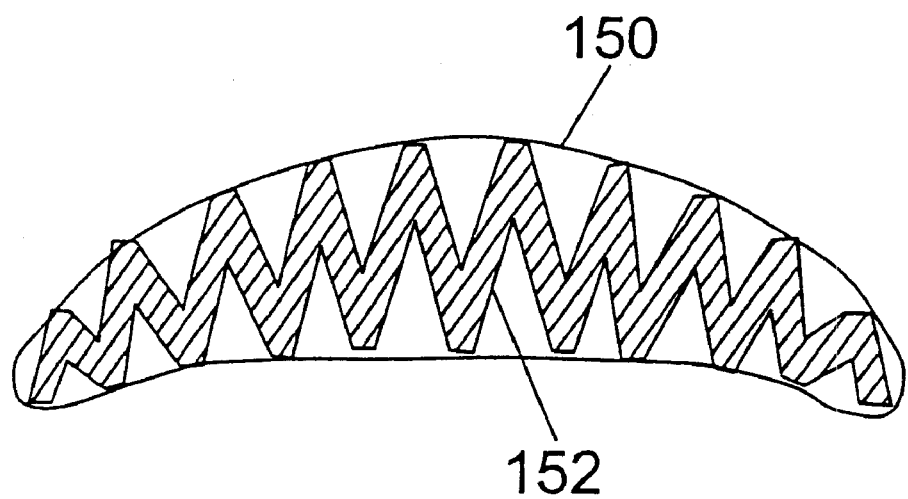
FIG. 7 illustrates a preferred method to scan a crescent-shaped treatment area according to the teachings of the present invention.

FIG. 5B illustrates a treatment pattern for the correction of astigmatism according to the teachings of the present invention. Two treatment areas 108 and 110 are placed at equal distances from the center of cornea 31 on the minus cylinder axis 112 of the manifest refraction. The treatment areas are preferably crescent-shaped as shown in FIG. 7. The arcuate long axis of the crescent conforms to a circle around the center of the cornea. Alternatively, the spindle shape may also be used. Shrinkage of collagen in the treatment areas shortens the cornea radially and steepens the central cornea along meridian 112 connecting the two treatment areas. The resulting radial tension on the treatment areas drives corneal remodeling and regression of refractive changes. According to the present invention, circumferential orientation of the long axes of the treatment areas spreads the restorative tension over greater lengths of corneal tissue and reduces regression. Prior art LTK methods for astigmatism correction use circular treatment areas or radially oriented shrunken collagen, thus exacerbating the problem of regression. Since astigmatic correction with prior art LTK methods has met with near-complete regression, the advantage of reduced regression is readily apparent.

The amount of astigmatism correction is primarily controlled by several parameters: (a) the width of the treatment areas, (b) the length of the treatment areas, and (c) the distance between the center of the cornea and the treatment areas. Smaller distances between the treatment areas and the center produce greater central corneal refractive change.

Figure 5C:
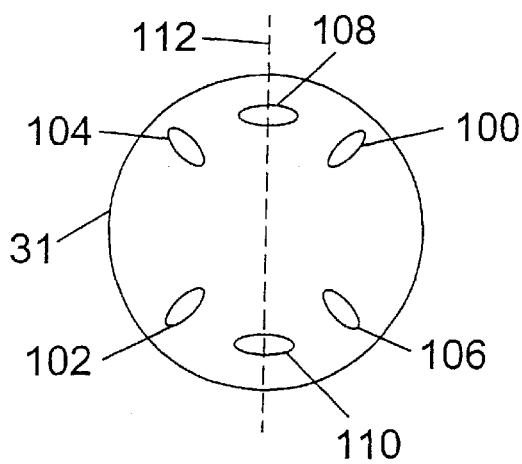
FIG. 5C illustrates a treatment pattern for the correction of combined hyperopia and astigmatism according to the teachings of the present invention.

FIG. 5C illustrates a treatment pattern for the correction of combined hyperopia and astigmatism according to the teachings of the present invention. The treatment pattern is a combination of those shown in FIG. 5A and FIG. 5B.

Figure 5D:
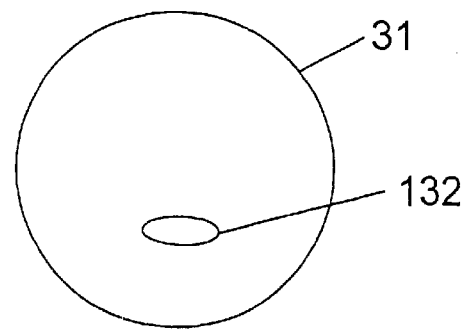
FIG. 5D illustrates a treatment pattern for the correction of an irregular corneal optical aberration according to the teachings of the present invention.

FIG. 5D illustrates a treatment pattern for the correction of an irregular corneal optical aberration according to the teachings of the present invention. Treatment area 132 is applied to an ectatic area on cornea 31. Ectasia is a term used to describe local bulging out of the cornea. Shrinkage of corneal tissue in the area of ectasia reduces the ectasia and the associated optical aberration. Clinical conditions where this is applicable includes keratoconus and pellucid marginal degeneration. In both diseases, the ectatic area tends to be inferior as shown in FIG. 5D. However, ectasia elsewhere on the cornea may be treated similarly.

FIG. 6 illustrates a parallel-lines scan pattern 142 that forms a confluent area of treatment 140 of a spindle shape. Also referring to FIG. 2, line 142 is produced by scanning laser beam 50 with steering mirrors 52 and 58 on cornea 31. FIG. 7 illustrates a wiggling scan pattern 152 that results in a confluent treatment area 150 of a crescent shape. Either scanning pattern can be applied to either treatment area shape. It is preferably to scan the beam in a way that produces uniform fluence in the treatment area. For example, in the pattern shown in FIG. 6, the horizontal line segments are preferably scanned at a uniformed rate, and the connecting diagonal line segments scanned much more rapidly. Other interrupted or continuous line patterns may also be used as long as laser heating is substantially evenly applied on the treatment area. The width of the scan line is the spot diameter of the focused treatment laser beam 42 on cornea 31. The laser spot size may be dynamically changed by adjusting the axial position of lenses in the path of treatment beam 42. However, for the sake of simplicity, the spot size is preferably fixed. The laser beam's intensity distribution at the focus is preferably Gaussian because this is the natural output pattern for most lasers. However, this is not essential to the application of the present invention. For a Gaussian laser beam, the spot size is conventionally defined as the diameter at which the intensity is $I/e^2$ of the central intensity. Because the intensity falls off toward the periphery of the beam, parallel segments of line 142 are preferably contiguous or overlapping by a fraction to produce uniform fluence in the treatment area. This overlap fraction is preferably between 0 and 0.5. Given a constant spot size, the width of the treatment area may be adjusted by varying the overlap fraction and the number of parallel line segments.

In order to confine shrinkage of the corneal tissue substantially within the irradiated area, the average dwell time of the laser beam is preferably equal to or less than the thermal diffusion time associated with the spot diameter. The dwell time is the time the laser takes to pass over a given position on the cornea. It is the spot diameter divided by the scan rate. The thermal diffusion time for a scanned line is similar to that of a long cylinder. Thermal diffusion time $t_r$ for a long cylinder of diameter d is $t_r = d^2/16 \kappa K$, where $\kappa$ is the thermal diffusivity, which for water is $1.3 \times 10^7$ m$^2$/sec (Anderson R R, Parsih J A, Selective photothermolysis: precise microsurgery by selective absorption of: pulsed radiation, *Science*, Vol. 220, pp. 524–527). As an example, for a spot diameter or line width of 250 microns, the diffusion time is approximately 30 msecs and the preferred scan rate is approximately 8 mm/sec or higher.

The fluence may be adjusted to raise the temperature in the anterior and mid-corneal stroma in the irradiated area to shrinkage temperature. Experimental fluence for corneal tissue in one literature source is 12 to 30 J/cm2 and 2.1 microns wavelength (Moreira, et al., Holmium Laser Thermokeratoplasty, *Ophthalmology*, Vol. 100, pages 752–761, 1993), using 1 pulse for the lower fluence and 3 pluses spaced 100 msec apart for the higher: fluence. As an example of a preferred treatment parameter according to the present invention, for a treatment area 0.6 mm wide and 1.5 mm long, the treatment area is approximately 0.7 mm$^2$. For 0.7 mm$^2$ treatment area, 20 J/cm2 fluence for each pass, and 0.5 W treatment laser power, the treatment time is 0.28 seconds. For a 250 micron spot size, the gives a scan rate of 10 mm/sec, which satisfies the thermal confinement requirement calculated above. To scan eight treatment areas, the combined treatment time is 2.2 seconds. Other treatment parameters may be used without departing from the teachings of the present invention. It is to be appreciated that in the present invention, the scanning method of laser delivery enables adequate thermal confinement using a laser power as low as 0.5 W, which is a considerable advantage over the prior art. However, prior art systems require numerous manual steps to form the novel treatment patterns taught in the present invention.

Figure 8:
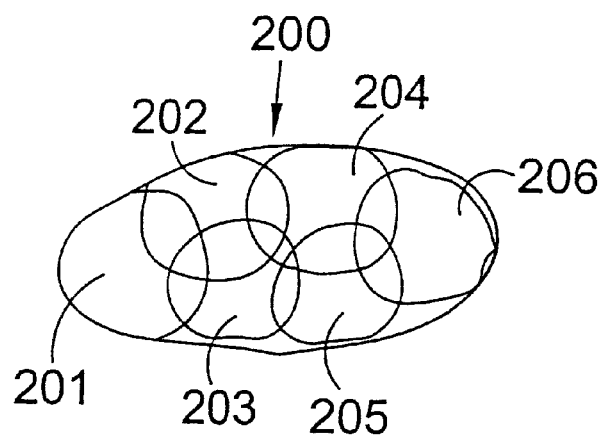
FIG. 8 illustrates a preferred method for forming an elliptically shaped treatment area using overlapping spots according to the present invention.

FIG. 8 illustrates a scan pattern that forms a confluent area of treatment 200 of a spindle shape. Also referring to FIG. 2, spots 201 to 206 are produced by scanning laser beam 50 with steering mirrors 52 and 58 on cornea 31. Spots of treatment are formed when the treatment laser 40 is a pulsed laser such as a Holmium laser. Multiple pulses may be delivered to each spot. It is desirable to distribute the laser energy deposited in each spot so that there is uniform fluence in the treatment area 200.

A preferred sequence for performing LTK using a preferred embodiment of the invention as described above is:

(a) Referring to FIG. 4, the treatment parameters are entered into computer 92 using input means 90 after considering clinical data such as manifest refraction, age, prior corneal procedures, keratometry and corneal topography.

(b) Referring to FIGS. 1 and 2, the patient is seated and the patient's head is stabley positioned relative to biomicroscope 23. The patient is instructed to fixate on beam 88.

(c) Referring to FIGS. 1 and 2, with treatment laser 40 off and aiming lasers 70 and 78 on, the laser surgeon positions laser apparatus 22 until dual focus beam 86 and 87 converge on central cornea and is centered relative to the pupil of eye 30.

(d) The laser surgeon initiates a trial run with aiming lasers on and treatment beam off while the planned scan pattern is executed. This tests the scanning system and patient cooperation.

(e) With both the aiming and treatment lasers enabled, the surgeon initiates the treatment sessions. The computer controls both the scanning system and the treatment laser output to produce the desired corneal treatment pattern.

(f) If patient movement is detected during treatment, the surgeon interrupts the treatment using an input means to the computer. Treatment is resumed after realignment of the laser apparatus and reestablishment of patient fixation.

FIGS. 9–12 illustrate a contact laser delivery system of another preferred embodiment of the present invention.

Figure 9:
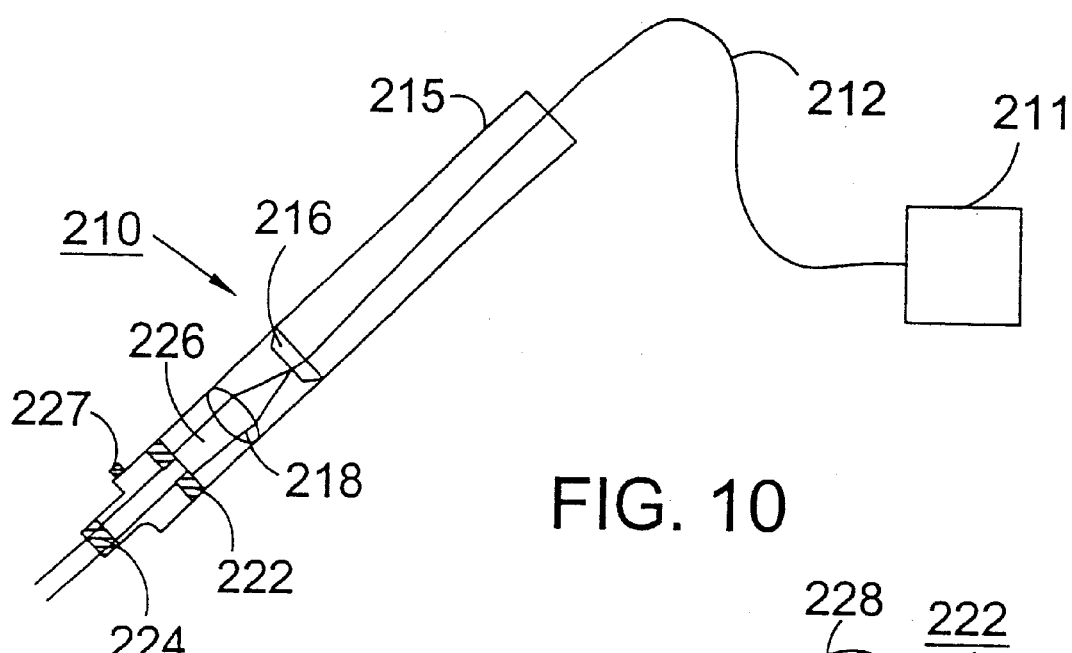
FIG. 9 is a cross-sectional view diagram showing a contact laser delivery probe of a preferred embodiment of the present invention.
Figure 10:
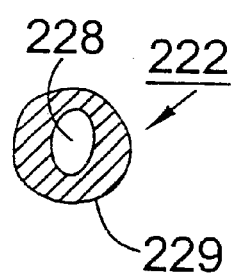
FIG. 10 illustrates the beam-shaping mask of a preferred embodiment of the present invention.

FIG. 9 illustrates a contact laser probe of a preferred embodiment of the present invention. Laser light from laser source 211 is channeled into optical fiber 212 which is in turn connected to the contact probe 210. The contact probe 210 has a tubular wall 215 which holds optical elements 218, 222, and 224. Fiber connector 216 secures optical fiber 212 to the probe. The laser beam 226 emitted from the fiber end is collimated by lens 218 and then shaped by mask 222. FIG. 10 illustrates the beam-shaping mask using an end face view. The mask 222 comprises a central aperture 228 surrounded by beam blocking material 229. Aperture 228 is preferably of a spindle shape or a crescent shape according to the present invention. Beam 226 then exits the probe tip through window 224. An alignment mark 227 on the outside of the probe tip is used for alignment to a fixation device.

Figure 11:
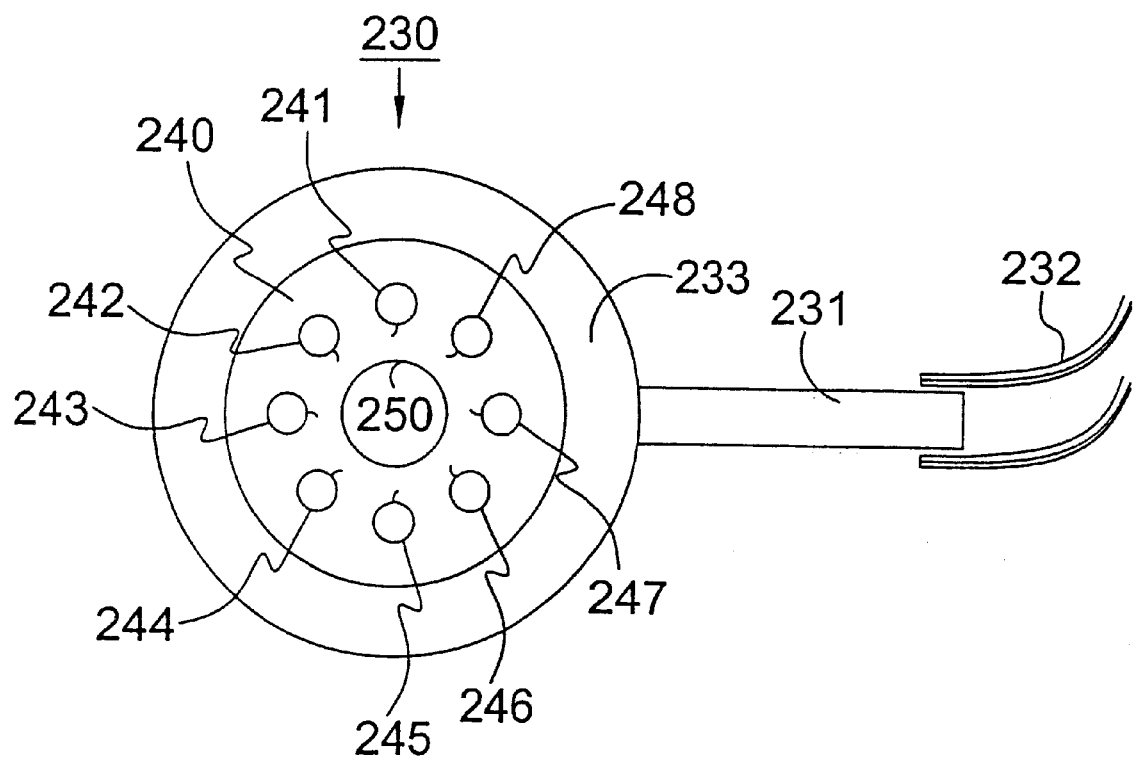
FIG. 11 is a top view diagram showing a fixation device of a preferred embodiment of the present invention.
Figure 12:
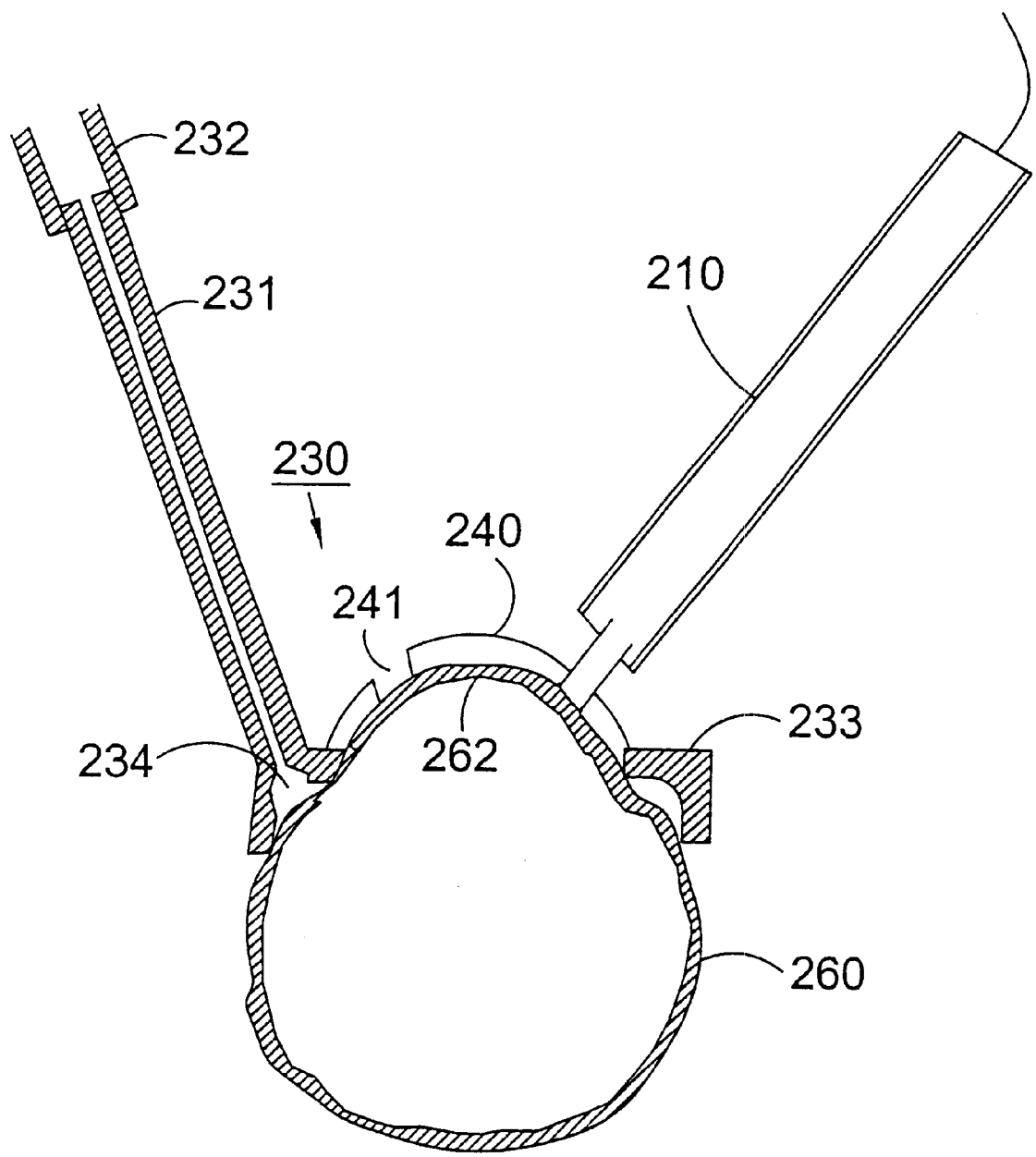
FIG. 12 is a cross-sectional view diagram showing a fixation device of a preferred embodiment of the present invention.

FIG. 11 and FIG. 12 illustrate a fixation device 230 used for positioning contact probe 210 (FIG. 9). Fixation device 230 has a handle 231 which has a lumen for transmitting vacuum suction. Vacuum tube 232 transmits suction from a vacuum source. Handle 231 is attached to suction ring 233. Suction hole 234 transmits vacuum to the space between suction ring 233 and eye 260. Applanation plate 240 is attached to the suction ring 233. Plate 240 is a clear dome with an under surface that is shaped to match the cornea 262. There is a centration marking 250 at the center of plate 240. Plate 240 has positioning holes 241–248 at the positions where laser treatment is to be delivered. Although eight holes in a circular distribution are shown in the illustration, other patterns may be used within the scope of the present invention. The pattern of laser application has been discussed earlier using FIG. 5A and 5B.

In operation, the fixation device 230 is placed in contact with eye 260, with the centration mark 250 centered on the pupil of the eye. The suction ring 233 is in contact with the eye around the cornea. Vacuum suction is turned on to secure the suction ring to the eye. Positioning holes 241–248 are used to guide the placement of contact probe 210. The distal tip of probe 210 is placed through holes 241–248 one at a time. The tip of the probe is placed in direct contact with the cornea through a positioning hole. Also referring to FIG. 10, the alignment mark 227 on the probe is aligned with a matching mark on the positioning hole. The marks preferably point toward the center of the cornea. Once the contact probe is positioned, laser energy is applied in one or more pulses. The probe 210 is then removed from corneal contact and placed through the next positioning hole. After laser treatment is delivered through the planned pattern of positioning holes, vacuum suction is stopped and the fixating device 230 is removed from the eye.

Although the above description contains many specificities, these should not be construed as limiting the scope of the invention but as merely providing illustrations of some of the presently preferred embodiments of this invention. Hence, numerous and additional modifications and variations of the present invention are possible in light of the above teachings. For example, a tracking device may be used with the invention to track eye movement.

The foregoing embodiments are merely exemplary and are not to be construed as limiting the present invention. The present teaching can be readily applied to other types of apparatuses. The description of the present invention is intended to be illustrative, and not to limit the scope of the claims. Many alternatives, modifications, and variations will be apparent to those skilled in the art. In the claims, means-plus-function clauses are intended to cover the structures described herein as performing the recited function and not only structural equivalents but also equivalent structures.

What is claimed is:

1. An apparatus for performing laser thermal keratoplasty on an eye of a patient to achieve an intended refractive correction, comprising:
   a treatment laser which outputs a treatment beam;
   a laser delivery device that projects laser energy of the treatment beam to the eye; and
   a controlling and processing device coupled to the laser delivery device, the controlling and processing device controlling the laser delivery device in a predetermined manner so that the treatment beam is delivered over at least one treatment area of the eye, wherein the at least one treatment area is at least one of elliptical, oval, and crescent shaped, and wherein a center of the at least one treatment area is positioned outside the optical zone of the eye.

2. The apparatus of claim 1, wherein the treatment area is elliptical or oval shaped.

3. The apparatus of claim 1, wherein the treatment area is crescent shaped.

4. The apparatus of claim 1, wherein the shape of the at least one treatment area extends along a first direction and a second direction perpendicular to the first direction, the at least one treatment area being longer in the first direction that in the second direction and being oriented so that the first direction is approximately along a radius stretching from a center of a cornea of the eye to a periphery of the cornea.

5. The apparatus of claim 1, wherein the shape of the at least one treatment area extends along a first direction and a second direction perpendicular to the first direction, the at least one treatment area being longer in the first direction than in the second direction and being oriented so that the first direction is approximately perpendicular to a radius stretching from a center of a cornea of the eye to a periphery of the cornea.

6. The apparatus of claim 1, wherein a shape of the at least one treatment area distributes stress over the at least one treatment area and areas surrounding the at least one treatment area in the cornea of the eye better than line-shaped or circular treatment areas.

7. The apparatus of claim 1, wherein the treatment beam has a wavelength such that collagen shrinkage occurs in a majority of a thickness of a cornea of the eye.

8. The apparatus of claim 1, further comprising:
   a power controlling device that controls a power level of the treatment beam and is coupled to the controlling and processing device;
   an aiming laser which outputs an aiming beam; and
   a beam combiner that combines the treatment beam and the aiming beam to yield a combined beam.

9. The apparatus of claim 1, wherein the laser delivery device comprises a scanning device that scans the treatment beam.

10. The apparatus of claim 9, further comprising:
    a power controlling device that controls a power level of the treatment beam and is coupled to the controlling and processing device;
    an aiming laser which outputs an aiming beam; and
    optics that receive the aiming beam and output dual focusing beams and a central fixation beam,
    wherein the controlling and processing device controls the scanning device so that the treatment beam is scanned over the at least one treatment area with a predetermined treatment beam power level when a central portion of the eye is aligned with the fixation beam.

11. An apparatus for performing laser thermal keratoplasty on an eye of a patient to achieve an intended refractive correction, comprising:
    a treatment laser which outputs a treatment beam;
    a laser delivery device that projects laser energy of the treatment beam to the eye; and
    a controlling and processing device coupled to the laser delivery device, the controlling and processing device controlling the laser delivery device in a predetermined manner so that the treatment beam is delivered over at least one treatment area of the eye, wherein the at least one treatment area is at least one of elliptical, oval, and crescent shaped, wherein a center of the at least one treatment area is positioned outside the optical zone of the eye, and wherein the laser device comprises a mask having a plurality of openings arranged such that the plurality of openings are for positioning around a pupil of the eye when the mask is in use.

12. An apparatus for performing laser thermal keratoplasty on an eye of a patient to achieve an intended refractive correction, comprising:
    a treatment laser which outputs a treatment beam;
    a laser delivery device that projects laser energy of the treatment beam to the eye; and
    a controlling and processing device coupled to the laser delivery device, the controlling and processing device controlling the laser delivery device in a predetermined manner so that the treatment beam is delivered over at least one treatment area of the eye, wherein the at least one treatment area is at least one of elliptical, oval, and crescent shaped, wherein a center of the at least one treatment area is positioned outside the optical zone of the eye, wherein the laser delivery device comprises a contact probe that contacts the eye and directs the treatment beam to the at least one treatment area, and wherein the contact probe has a mask internal to the contact probe, the mask having an opening through which the treatment beam passes, the opening being at least one of elliptical, oval, and crescent shaped.

13. The apparatus of claim 12, wherein the opening is elliptical or oval shaped.

14. A method of performing laser thermal keratoplasty on an eye of a patient to achieve an intended refractive correction, comprising:

outputting a treatment beam from a treatment laser;

projecting laser energy of the treatment beam to the eye in at last one treatment area, wherein the at least one treatment area at least one of elliptical, oval, and crescent shaped, and wherein a center of the at least one treatment area is positioned outside the optical zone of the eye.

15. The method of claim 14, wherein the treatment area is elliptical or oval shaped.

16. The method of claim 14, wherein the treatment area is crescent shaped.

17. The method of claim 14, wherein the laser energy is projected to the eye by scanning the treatment beam over the at least one treatment area.

18. A method of performing laser thermal keratoplasty on an eye of a patient to achieve an intended refractive correction, comprising:

outputting a treatment beam from a treatment laser;

projecting laser energy of the treatment beam to the eye in at last one treatment area, wherein the at least one treatment area at least one of elliptical, oval, and crescent shaped, and wherein a center of the at least one treatment area is positioned outside the optical zone of the eye, wherein the laser energy is projected to the eye through a mask, the mask having at least one opening, the opening being approximately the shape of the at least one treatment area.

19. A method of performing laser thermal keratoplasty on an eye of a patient, comprising:

outputting a central fixation beam with a fixation laser;

aligning the central fixation beam with a predetermined portion of the eye; and outputting a treatment beam with the treatment laser, wherein the treatment beam projects laser energy to the eye in at least one treatment area, and the at least one treatment area is at least one of elliptical, oval, and crescent shaped, a center of the at least one treatment area being positioned outside the optical zone of the eye.

20. The method of claim 19, wherein the treatment area is elliptical or oval shaped.

21. The method of claim 19, wherein the treatment area is crescent shaped.

22. The method of claim 19, wherein the laser energy is projected to the eye by scanning the treatment beam over the at least one treatment area.

23. The method of claim 19, wherein the shape of the treatment area distributes stress caused by collagen shrinkage to be distributed over the eye better than line shaped treatment areas.

* * * * *